United States Patent [19]
Gelbard

[11] Patent Number: 5,888,221
[45] Date of Patent: Mar. 30, 1999

[54] SPINAL STABILIZATION IMPLANT SYSTEM

[76] Inventor: Steven D. Gelbard, 8130 Royal Palm Blvd. Suite. 200, Coral Springs, Fla. 33065

[21] Appl. No.: 949,804

[22] Filed: Oct. 14, 1997

Related U.S. Application Data

[62] Division of Ser. No. 241,356, May 11, 1994, abandoned, which is a division of Ser. No. 928,263, Aug. 11, 1992, Pat. No. 5,397,363.

[51] Int. Cl.$^6$ ..................................................... A61F 2/44
[52] U.S. Cl. ............................................... 623/17; 606/61
[58] Field of Search ............................... 623/17; 606/61, 606/62, 63, 64, 75

[56] References Cited

U.S. PATENT DOCUMENTS

| | | | |
|---|---|---|---|
| 5,154,719 | 10/1992 | Cotrel | 606/73 |
| 5,176,680 | 1/1993 | Vignaud | 606/73 |
| 5,360,431 | 11/1994 | Puno | 606/73 |
| 5,474,555 | 12/1995 | Puno | 623/17 |
| 5,487,742 | 1/1996 | Cotrez | 606/61 |
| 5,527,315 | 6/1996 | Jeanson | 606/61 |
| 5,620,443 | 4/1997 | Gertzbein | 606/61 |

FOREIGN PATENT DOCUMENTS

| | | | |
|---|---|---|---|
| 348272 | 12/1989 | European Pat. Off. | 623/17 |

*Primary Examiner*—Michael J. Milano
*Attorney, Agent, or Firm*—McHale & Slavin, P.A.

[57] ABSTRACT

A surgical implant system for the stabilization of a human spine by fixation of the vertebra utilizing a stabilization cross-link spinal implant system. The system utilizes self-tapping screws having bifurcated protruding members to support an alignment rod, the protruding members available for placement of a fixed or variable traverse cross-link member that couples to the protruding members by use of threaded nuts corresponding to the threaded portion of the outer surface of the protruding members. The externally threaded coupling method can also be use for pedicle, caudal, cranial, thoracic and the like hooks. Also shown is a two plate system for anterior cervical spine fixation.

5 Claims, 1 Drawing Sheet

SPINAL STABILIZATION IMPLANT SYSTEM

This is a divisional of 08/241,356, now abandoned, filed May 11, 1994 which is a divisional of 07/928,263, filed Aug. 11, 1992 which is as U.S. Pat. No. 5,397, 363 on Mar. 14, 1995.

BACKGROUND OF THE INVENTION

1. Field of the Invention

This invention relates generally to spinal implants and, in particular, to a spinal implant having a novel top-loading bolt attachment for support and alignment rods with cross links and ancillary components for stabilization of the vertebrae as well as a two plate system for cervical spine fixation.

2. Background of the Invention

Surgical implants are well known in the art for treatment of curvatures of the spine including anterior, trauma, deformity, and/or degenerative spinal conditions. The purpose of the implant is to reinforce the spine by use of strategically placed attachment screws capable of supporting alignment support rods placed bilateral along the vertebrae as well as cross-link members that bridge the sagittal of the spine.

The problem which this invention addresses is the method of fastening the spinal implants during surgery. Conventionally, the placement of an attachment screw provides the functional base for the support rod, cross-link, caudal facing hooks, cranial facing hook and the like components that form a spinal implant system. The conventional method of fastening utilizing a goal post mounting screw from which a bolt and nut is coupled perpendicular thereto for mounting to the component. This side attachment frequently requires the movement of muscle and other tissue during operation which increases the difficulty of the operation, is a time consuming effort, and can be a major trauma to a person.

In addition, the use of the prior art devices required pre-thought to where the cross-links are to be placed. Once the base screws are installed, they cannot be moved and if the screws are placed incorrectly, the cross-link will not fit.

U.S. Pat. No. 5,084,048, issued to Jacob et al., entitled "Implant for Vertebrae With Spinal Stabilizer" discloses a vertebrae implant having a stabilizing element which is articulated to accommodate a pair of bone screws wherein each bone screw includes a clamp disposed between a shoulder in a spherical surface which is all coupled together by the use of a clamping nut directly on the end of the bone screw. The device allows for support of an alignment rod along the side of the bone screw, but fails to provide any type of cross link or ancillary component attachment devices.

U.S. Pat. No. 4,041,939, issued to Hall, entitled "Surgical Implant Spinal Screw" discloses a spinal implant utilizing a screw having a centrally disposed aperture for placement of a metal cable therethrough with a nylon insert that will permanently secure the cable in a fixed position once attached. The device is best used in an operation for the correction of scoliosis.

Another problem with prior art is the use of anterior cervical plates. The prior art employs a single plate that is attached by the use of small bone attachment screws. After installation, the screws have a tendency of working their way out of the bone resulting in the loosening of the cervical plate causing the patient pain and typically resulting in further surgery to correct the problem.

Therefore there exists a need to correct the aforementioned problems by use of a top loading spinal implant system and associated cervical plate attachment cover.

SUMMARY OF THE INVENTION

The instant invention is a surgical implant system for the stabilization of the human spine by fixation of the vertebra. The system is based upon screws, nuts, rods, hooks, cross-members and variations thereof. The preferred embodiment employs a metal screw for placement in the sacrum or pedicle defined by a coarse self-tapping thread and a U-shaped saddle for placement of conventional alignment rods. Unique to this invention is that the screw is threaded on the outer surface of the saddle allowing the alignment rod to be securely fastened into the saddle by placement of the rod therein and the fastening of a nut to the top of saddle. Further unique to this invention is the use of an elongated sagittal traverse support member that can accommodate the saddle protrusion either in a fixed position or by use of a rotatable insert that allows the cross member to be tightly fastened to the saddle in a variable alignment. The top-loading attachment is further applicable to caudal, cranial, and the like hook components.

An anterior cervical plate is set forth using a second plate to permanently lock the cervical plate in position. The second plate does not rely upon the bone to support the plate thus providing a means to prevent any bone attachment screws from loosening or otherwise backing out of the bone.

Accordingly, an objective of the instant invention is to provide thoracic lumbar stabilization by use of linking conventional support alignment rods placed bilaterally along the vertebrae with the top-loading sacral and pedicle screws of the instant invention.

Still another objective is to lessen the need for ancillary tissue movement during surgery by use of a top mounted attachment means for ancillary components and provide a variable attachment system to provide the surgeon with fixation components that will accommodate a variety of circumstances.

Yet another objective of the instant invention is to provide a cross-link member that is operatively associated with the attachment screws by means of a top mounted link that is receptive to the protruding members of the screws or separate cross link attachments.

Yet still another objective of the instant invention is to provide a variable attachment means for two member and four member attachment screws by the use of rotatable attachment slots within the cross-link members.

Still another objective of the instant invention is to simplify the means for attaching caudal, thoracic, cranial and the like hooks by use of a top loading fastening nut that is threaded directly onto the hook body.

Still another objective of the instant invention is to provide an improved sacral and pedicle pinion post screw that allows angular bridging by use of an indexing right angled base having the means for coupling to another right angled base.

Yet still another objective is to disclose an improved anterior cervical plate having a second plate that couples to the cervical mounted plate effectively locking the cervical mounted plate in position by preventing the retraction of the mounting screws, while allowing the mounting screws to be put in at various angles and positions.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the instant invention and illustrate various objects and features thereof.

DETAILED DESCRIPTION OF THE PREFERRED EMBODIMENT

As required, detailed embodiments of the present invention are disclosed herein, however, it is to be understood that the disclosed embodiments are merely exemplary of the invention which may be embodied in various forms. Therefore, specific functional and structural details disclosed herein are not to be interpreted as limiting, but merely as a basis for the claims and as a representative basis for teaching one skilled in the art to variously employ the present invention in virtually any appropriately detailed structure.

Figure 1:
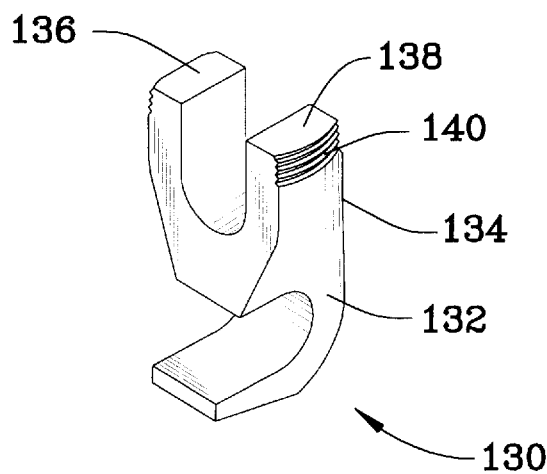
FIG. 1 is a perspective view of the bifurcated externally threaded hook attachment.
Figure 2:
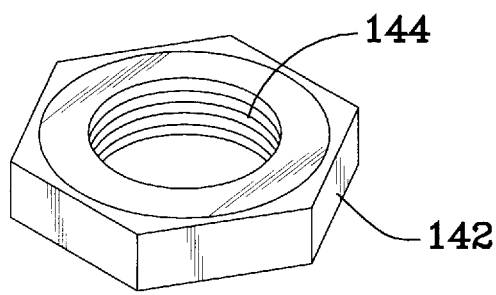
FIG. 2 is a perspective view of the attachment nut for use with the spinal screw of FIG. 1.

FIGS. 1 and 2 illustrate a perspective view of a caudal facing hook 130 having a hook shaped base 132 formed integral with a saddle shaped upper portion 134. The saddle shape portion illustrates the protruding member 136 and 138 common to the invention with the threads 140 cast into the outer surface of the members. The saddle in this type of hook allows for attachment directly onto an alignment support rod wherein the metal nut 142 includes internal threads 144 engageable directly with the hook body 130 threads 140 securely fastening the hook in position. Although not shown, but deemed a part of this invention, is the use of various hook embodiments such as claw and fork hook which employ the top-loading threaded attachment of the instant invention. Unique to this invention is the ability to top-load the screw, attachment device, or hook member allowing the surgeon to perform all couplings from directly above the spine, as compared to the prior art requiring the attachment from the side. The importance of this factor cannot be emphasized enough, or illustrated by drawings, as the amount of muscle that encompasses the spinal area must be moved to accommodate the prior art attachment methods.

Figure 3:
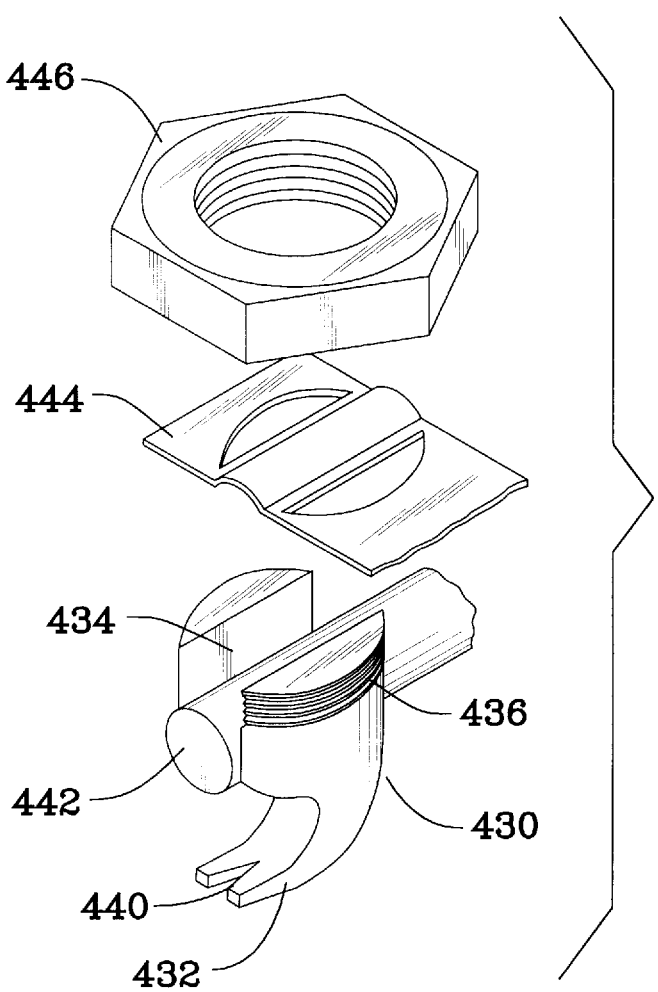
FIG. 3 is a perspective view of an enlarged bifurcated externally threaded hook attachment with a preformed support member.

FIGS. 3 provides a perspective view of an oversized caudal facing hook 430 having a hook shaped base 432 with a fork opening 440 formed integral with a saddle shaped upper portion 434. The saddle shape portion illustrates the enlarged protruding member necessary in instances of large bone attachment or the need of greater strength. The embodiment utilizes a form of four member protrusion with the U-shaped side surfaces thereby providing the additional support. The saddle allows for attachment directly onto an alignment support rod wherein the metal nut 446 includes internal threads engageable directly with the threaded hook body 436. The nut 446 forcing the support plate 444 tightly against the alignment rod 442, the use of a beveled support plate is shown 444 which is preformed to accommodate the curvature of the rod thereby allowing an increase in the surface area of contact.

It is to be understood that while we have illustrated and described certain forms of our invention, it is not to be limited to the specific forms or arrangement of components herein described and shown. It will be apparent to those skilled in the art that various changes may be made without departing from the scope of the invention and the invention is not to be considered limited to what is shown in the drawings and described in the specification.

What is claimed is:

1. A device for use in a surgical implant system for the stabilization of a human spine by fixation of the vertebra, said device comprising:

an attachment member defined by an upper portion having at least two spaced-apart protruding members forming an inner surface saddle configured for receipt of at least one rod therein and a lower portion including a hook-shaped attachment flange, at least one of said protruding members having an outer threaded surface;

a means for securing said attachment member to said rod; and a support plate having a raised portion contoured to engage an outer surface of said rod, said support plate being perforated to accept said protruding members; said support plate including flanges oriented orthogonal to a central axis of a said rod, said flanges cooperating with said means for securement to apply compressive force to said rod and said protruding members when said means for securement is screwed onto said threaded surface;

whereby a linking alcove is formed between said attachment members and said rod, and wherein said attachment flange is adapted to encircle a portion of one of said vertebra.

2. The attachment member of claim 1, wherein said attachment flange includes a forked free end.

3. The attachment member of claim 1, wherein said attachment flange has a claw-shaped free end.

4. The attachment member of claim 1, wherein said securement means is a nut sized to selectively engage said outer threaded surface of said upper portion.

5. The attachment member of claim 1 wherein said protruding members have an enlarged circular shape sized to engage a substantial portion of an attachment nut.

* * * * *